(12) United States Patent
Haase et al.

(10) Patent No.: US 12,380,562 B2
(45) Date of Patent: Aug. 5, 2025

(54) VESSEL REGISTRATION USING FUNCTIONAL INFORMATION

(71) Applicant: KONINKLIJKE PHILIPS N.V., Eindhoven (NL)

(72) Inventors: Christian Haase, Hamburg (DE); Martijn Anne Van Lavieren, Abcoude (NL); Michael Grass, Buchholz In der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 376 days.

(21) Appl. No.: 17/622,285

(22) PCT Filed: Jun. 23, 2020

(86) PCT No.: PCT/EP2020/067390
§ 371 (c)(1),
(2) Date: Dec. 23, 2021

(87) PCT Pub. No.: WO2020/260219
PCT Pub. Date: Dec. 30, 2020

(65) Prior Publication Data
US 2022/0262000 A1      Aug. 18, 2022

(30) Foreign Application Priority Data

Jun. 28, 2019   (EP) ..................................... 19183270

(51) Int. Cl.
*G06T 7/00*        (2017.01)
*G06F 30/28*       (2020.01)
*G06T 7/70*        (2017.01)

(52) U.S. Cl.
CPC ............ *G06T 7/0016* (2013.01); *G06F 30/28* (2020.01); *G06T 7/70* (2017.01); *G06T 2207/20081* (2013.01); *G06T 2207/30104* (2013.01)

(58) Field of Classification Search
CPC ....................................................... G06T 7/00
See application file for complete search history.

(56) References Cited

U.S. PATENT DOCUMENTS

2009/0074267 A1   3/2009   Pedrizzetti
2011/0060755 A1   3/2011   Mollus
(Continued)

FOREIGN PATENT DOCUMENTS

IN    3021/CHE/2015        12/2016
WO    2015106197 A2         7/2015
WO    WO-2017017086 A1 *    2/2017    ........... A61B 6/4441

OTHER PUBLICATIONS

International Search Report and Written Opinion of PCT/EP2020/067390, dated Aug. 26, 2020.
(Continued)

*Primary Examiner* — Di Xiao (57) ABSTRACT

A method and apparatus for analyzing diagnostic image data are provided in which correspondence detection between a first diagnostic image and a second diagnostic image of a vessel of interest in a patients vasculature is performed on the basis of at least one functional parameter by matching the one or more values of said functional parameter at particular positions along the vessel of interest as shown in the first diagnostic image and the second diagnostic image to one another, thereby determining a correlation between the positions in the basis of said functional parameter values rather than solely the vessel geometry.

23 Claims, 4 Drawing Sheets

(56) References Cited

U.S. PATENT DOCUMENTS

| | | |
|---|---|---|
| 2014/0121513 A1 | 5/2014 | Tolkowsky |
| 2014/0206414 A1 | 7/2014 | Oh |
| 2015/0020157 A1 | 1/2015 | Kim |
| 2016/0051218 A1* | 2/2016 | Ohishi .................. G06T 7/11 |
| | | 600/431 |
| 2016/0247325 A1* | 8/2016 | Yu ........................ H04N 5/32 |
| 2017/0091927 A1 | 3/2017 | Auvray |
| 2018/0184911 A1 | 7/2018 | Lavi |
| 2018/0195038 A1* | 7/2018 | Matsumoto ............ G01N 33/48 |
| 2018/0288753 A1 | 10/2018 | Kishiyama |
| 2019/0076105 A1* | 3/2019 | Haase .................. A61B 6/5217 |
| 2019/0126008 A1* | 5/2019 | Breininger ............... G06T 7/70 |
| 2019/0189286 A1* | 6/2019 | Grady ................... G16H 10/20 |
| 2019/0357778 A1* | 11/2019 | Wilson .............. A61M 5/16831 |
| 2022/0015730 A1* | 1/2022 | Haase ................... A61B 6/481 |
| 2022/0107256 A1* | 4/2022 | Buoso ................... G16H 30/40 |

OTHER PUBLICATIONS

Granero, M.A. et al "An Alternative Technique for Imaging Registration in IVUS Images", 2015 International Confierence on Computation Science and Computational Intelligence.

* cited by examiner

VESSEL REGISTRATION USING FUNCTIONAL INFORMATION

CROSS-REFERENCE TO PRIOR APPLICATIONS

This application is the U.S. National Phase application under 35 U.S.C. § 371 of International Application No. PCT/EP2020/067390, filed on Jun. 23, 2020, which claims the benefit of European Patent Application No. 19183270.8, filed on Jun. 28, 2019. These applications are hereby incorporated by reference herein.

FIELD OF THE INVENTION

The present invention relates to a method for analyzing diagnostic image data, in some embodiments multi-modality diagnostic image data, a corresponding apparatus and a respective computer program. In particular, the present invention relates to an improved method and apparatus that allows to more reliably and accurately perform correspondence detection for a vessel of interest in a patient's vasculature as represented in multiple diagnostic images by using functional parameter values.

BACKGROUND OF THE INVENTION

Nowadays, coronary artery disease is a widely-spread ailment in many societies. In order to establish appropriate treatment options for each individual patient, it is of vital importance to obtain as much information about the coronary vasculature as possible. Hereby, an accurate assessment of the geometric properties of the vasculature as well as the hemodynamic properties through the vasculature with sufficient reliability is particularly relevant.

To that end, a multitude of different medical measurement modalities are known to obtain the respective medical data regarding these properties. Amongst those are medical imaging modalities such as Computed Tomography (CT) angiography, invasive angiography, Intravascular Ultrasound (IVUS) imaging, Magnetic Resonance (MR) imaging, Intracardiac Echocardiography (ICE), Transesophageal Echocardiography (TEE) or the like, as well as fluid dynamics measurement modalities such as invasive Functional Flow Reserve (FFR) or Instantaneous Wave-Free Ratio (IFR) measurements, ultrasonic flow measurements, such as Doppler flow measurements or the like.

Each of the medical imaging modalities hereby allows to gather specific diagnostic image data revealing specific information about the vasculature. This specific information may differ from imaging modality to imaging modality and even from diagnostic image to diagnostic image acquired using the same imaging modality, as acquisition settings such as projection direction, cardiac motion and the like may change the visualization of the vasculature in the different diagnostic images.

As such, in order to perform an accurate and reliable assessment of the vasculature and, hence, any potential (coronary) artery disease, it is beneficial to use not only a single diagnostic image, but to use a combination of multiple diagnostic images in order to retrieve a more complete picture of the vasculature.

Accordingly, methods have been developed in which a plurality of different diagnostic images are correlated with one another such as to retrieve more information about the coronary arteries. Applications which allow such correlation are e.g. vascular road map co-registration, image fusion for different imaging modalities or motion compensated vascular modeling.

Hereby, in order to properly combine the different diagnostic images, the so-called correspondence detection has to be performed during which the same vessel of interest—or segment thereof—is identified in all diagnostic images and, thus, is co-registered for all diagnostic images. That is, it is determined which vessel (segment) in a first diagnostic image corresponds to which vessel (segment) in a second diagnostic image.

However, an accurate correspondence detection is often prevented by factors such as changed projection direction, cardiac motion, the usually non-calibrated C-arm geometry or the like. As an example, in two or more two-dimensional angiograms acquired from different projection directions, the same vessel (segment) may appear to have so different properties that a correspondence between the vessel (segment) as represented in the first diagnostic image and the same vessel segment as represented in the second diagnostic image may only be established with low accuracy. This issue becomes even more severe in cases where the diagnostic images are acquired using different imaging modalities. As an example, the co-registration of a CT angiogram with invasive angiography data shall be mentioned. Such registration of the CT angiogram to the angiography data may be very challenging since cardiac motion and/or unknown relative geometry may cause ambiguities.

Thus, various feature detection modes have been developed which supposedly allow to accurately determine these correspondences. These feature detection modes are typically based on the combination of many features like bifurcation locations, characteristic curves, geometry constraints or the like. Using these features often results in the most robust correspondence.

Despite this, an approach that allows for a particularly accurate and reliable correspondence establishment between the same vessel (segment) as represented in different diagnostic images has not yet been developed.

SUMMARY OF THE INVENTION

It is therefore an object of the invention to provide a method and an apparatus that enables correspondence detection for one or more vessel segments of a vasculature in a reliable, accurate and efficient manner.

More particularly, it is an object to provide a method and apparatus for analyzing diagnostic image data that allows to combine multiple diagnostic images by performing a reliable correlation between the individually used diagnostic images.

It is a further object to provide a method and apparatus that allows to perform multi-modality image visualization and/or multi-modality modelling of a patient's vasculature—that is, one or more vessels or vessel segments therein—in a reliable and accurate manner.

This object is achieved by a method for analyzing diagnostic image data which comprises the steps of obtaining a first diagnostic image and a second diagnostic image of a vessel of interest in a patient's vasculature, defining at least one determination position for the vessel of interest in the first diagnostic image and at least one corresponding determination position for the vessel of interest in the second diagnostic image, determining a first value for at least one functional parameter at the least one determination position for the first diagnostic image and a second value for the same at least one functional parameter at the corresponding determination position for the second diagnostic image, correlating one or more vessel positions along the vessel of interest as represented in the first diagnostic image with one or more vessel positions along the vessel of interest as represented in the second diagnostic image based on a comparing of the first value of the at least one functional parameter and the second value of the at least one functional parameter.

That is, two diagnostic images are co-registered to one another on the basis of a functional parameter that has been determined for at least one particular determination position in both diagnostic images.

In that context, the term diagnostic image may particularly refer to an image representing the patient's vasculature. Hereby, the term vasculature may refer to a vessel tree or a single vessel. The term vasculature may particularly refer to a vessel segment of the vessel of interest. In some embodiments, the diagnostic image may represent a vasculature including one or more vessels of interest of the coronary vasculature.

The first diagnostic image and the second diagnostic image may particularly be obtained by a diagnostic imaging modality. The diagnostic imaging modality may particularly be gated. Hereby, the gated diagnostic imaging modalities may typically employ a gated reconstruction, in which the acquisition of the diagnostic images is performed in parallel with acquisition of data providing information over the cardiac cycle, such as electrocardiogram (ECG) or photoplethysmographic (PPG) data. This data may hereby be used to gate the image acquisition and the reconstruction by means of respectively selected phase points of the cardiac cycle.

The term determination position may particularly refer to a particular position along the vessel of interest as represented in the first diagnostic image and in the second diagnostic image at which a value for a functional parameter may be determined, e.g. by an actual invasive measurement, such as an intravascular pullback measurement and/or a non-invasive measurement, such as a Doppler flow measurement, and/or by simulating the fluid dynamics through the vessel of interest using a respective fluid dynamics model. A plurality of determination positions may be used, at each of which a corresponding value for one or more functional parameters may be determined.

The term functional parameter may particularly refer to parameters that are indicative of the dynamic behavior of the vessel of interest, in particular of the fluid dynamics through the vessel of interest. That is, functional parameters may refer to parameters such as pressure, flow, vascular resistance or the like which vary alongside a vessel of interest.

The term vessel position may particularly refer to a position along the vessel of interest. A plurality of vessel positions may be determined along a length of the vessel of interest. The vessel positions in the first diagnostic image and the second diagnostic image are correlated to one another by comparing the first and the second value of the at least one functional parameter obtained for the determination position in the first diagnostic image and the determination position in the second diagnostic image.

That is, if a plurality of first values is obtained for a particular functional parameter in the first diagnostic image and a plurality of second values is obtained for the same functional parameter in the second diagnostic image, these values may be compared to one another. The determination positions for which the values correspond to one another are then correlated to one another, i.e. are assumed to correspond to the same vessel position as represented in the two images.

Thus, in accordance with the method, at least one determination position is determined in both diagnostic images. Subsequently, a value of a functional parameter is determined for the at least one determination position. The thus determined values, determined for the first diagnostic image and the second diagnostic image, respectively, are then compared to one another in order to establish a correlation. As an example, if the value for one particular determination position in the first diagnostic image corresponds to the value for one particular determination position in the second diagnostic image, these determinations positions are assumed to correspond to the same vessel position inside the vessel of interest due to exhibiting the same value for a particular functional parameter. This allows to perform correspondence detection between the first diagnostic image and the second diagnostic image, even in cases where the diagnostic images have been acquired using different acquisition settings and/or different imaging modalities.

In some embodiments, the obtaining of the first diagnostic image and the second diagnostic image comprises acquiring the first diagnostic image by a first diagnostic imaging modality using a first acquisition setting, and acquiring the second diagnostic image by the first diagnostic imaging modality using a second acquisition setting, different from the first acquisition setting.

In some embodiments, the first diagnostic image and the second diagnostic images may have been acquired using one particular diagnostic—or medical—imaging modality such as CT angiography, invasive angiography, IVUS imaging, MR imaging, ICE, TEE or the like with differing acquisition settings. In one particular embodiment, the first diagnostic image and the second diagnostic image may be acquired using two-dimensional X-ray angiography with two different acquisition settings, respectively.

In that context, the term acquisition settings may particularly refer to the setting of acquisition parameters, such as radiation time, projection direction, acquisition timing relative to the cardiac cycle or the like, that may be adjusted from patient to patient, or even from image to image. A change in acquisition setting thus corresponds to the change of one or more acquisition parameters for performing the respective acquisition. Such a change typically results in a change of the representation of the vessel of interest in the diagnostic image.

Thus, using different acquisition settings to acquire two or more diagnostic images and subsequently correlating these images to one another allows for gathering more information about the vessel of interest or a segment thereof.

In some embodiments, the obtaining of the first diagnostic image and the second diagnostic image comprises acquiring the first diagnostic image by a first diagnostic imaging modality, and acquiring the second diagnostic image by a second diagnostic imaging modality, different from the first diagnostic imaging modality. In some embodiments, the first diagnostic imaging modality corresponds to a non-invasive diagnostic imaging modality and the second diagnostic imaging modality corresponds to an invasive diagnostic imaging modality.

In some embodiments, the first and second diagnostic image may also be acquired using different imaging modalities. As an example, the first diagnostic image may have been acquired using a non-invasive imaging modality, such as CT angiography, X-ray angiography, MR imaging, US imaging or the like, and the second diagnostic image may have been acquired using an invasive imaging modality, such as invasive angiography, IVUS imaging, ICE or TEE imaging or the like. In other embodiments, both, the first and the second diagnostic image may be acquired using an invasive imaging modality or both, the first and the second diagnostic image may be acquired using a non-invasive imaging modality. It shall further be understood that the respective acquisition settings may particularly depend on the individual imaging modalities used.

Since each imaging modality allows to visualize different aspects of the vessel of interest, the use of different imaging modalities allows to gather more information than would be available from the use of a single imaging modality. By using the functional parameter values for correlating between the first diagnostic image and the second diagnostic image, correspondence detection of the vessel of interest in the first diagnostic image and the second diagnostic image, respectively, is still possible irrespective of the different imaging method used for acquiring them. This is the case since the functional parameters are related to the dynamics of the vessel of interest and not (primarily) to the geometric properties—which may be represented differently when using different imaging modalities. In particular, the combination of non-invasive and invasive techniques allows to acquire a wide variety of information about the vessel of interest. This improves the accuracy of the vessel assessment and, hence, the diagnosis of any possible ailments.

In some embodiments, the determining of the first value and/or the second value of the at least one functional parameter comprises acquiring intravascular measurement data for the vessel of interest, and deriving, based on the intravascular measurement data, the first and second value of the at least one functional parameter at the at least one determination position. In some embodiments, the determining of the first value and/or the second value of the at least one functional parameter comprises generating a fluid dynamics model for the vessel of interest, and deriving, based on the fluid dynamics model, the first and second value of the at least one functional parameter at the at least one determination position.

In some embodiments, the functional parameter values may particularly be derived from an invasive measurement of said functional parameter. For that purpose, a catheter or the like having a respective measurement device attached thereto may be introduced into the patient's vasculature and, in particular, into the vessel of interest. Inside the vessel of interest, the measurement device may be used to acquire intravascular measurement data, such as values for one or more of a pressure, a flow, a vascular resistance or the like at dedicated positions along the length of the vessel of interest.

In some embodiments, the first value of the at least one functional parameter may have been determined using first intravascular measurement data having been acquired by a first measurement modality and the second value of the at least one functional parameter may have been determined using second intravascular measurement data having been acquired by a second measurement modality.

Further, in some specific embodiments, the measurement data collected for the vessel of interest in the first diagnostic image and for the vessel of interest in the second diagnostic image may correspond to pullback data, such as pressure pullback data. The pullback data may then comprise a plurality of first functional parameter values, one for each measurement position, i.e. each position at which a pullback measurement was performed, in the vessel of interest as shown in the first diagnostic image. The pullback data may further comprise a plurality of second functional parameter values, one for each measurement position in the vessel of interest as shown in the second diagnostic image.

In some embodiments, the functional parameter values may be derived from respective fluid flow simulations using a fluid dynamics model representing the blood flow through the vessel of interest and/or a blood flow through multiple vessels in the vasculature. The term fluid dynamics model may hereby particularly refer to a model of the blood flow through the vessel of interest.

This fluid dynamics model is generated by simulating the interaction of the blood with the vessel wall. Since the blood is a fluid and the vessel walls may be considered respective surfaces with which the fluid interacts, the interaction of the blood with the vessel walls may most accurately be defined by respective boundary conditions that take account of the properties of the vessel wall and the blood interacting with it. These properties may include vessel wall composition, vessel wall elasticity and vessel impedance, bifurcations in the vessel, outflow through these bifurcations, blood viscosity, the vessel outlet resistance at certain positions along the length of the vessel and the like. The fluid dynamics model may be integrated with a two- or three-dimensional geometric model and hereby represents the fluid dynamics of the blood at each position in the vessel or vessels of interest shown in the geometric model.

In some embodiments, one—for example the first—functional parameter value may correspond to a measured value whereas the other—for example the second—functional parameter value may correspond to a simulated value, having been simulated by means of the fluid dynamics model. As an example, the first functional parameter value may be obtained using a pullback measurement, such as a pressure, in particular FFR or iFR, pullback measurement, an ultrasonic flow measurement, such as a Doppler flow measurement, or the like and the second functional parameter may be obtained by means of simulating the corresponding function parameter using a fluid dynamics model.

In that context, in some exemplary embodiments, the first diagnostic image may correspond to a CT angiography image and the second diagnostic image may correspond to an invasive angiography image, whereby the first functional parameter values for the first diagnostic CT angiography image correspond to simulated iFR values derived from a fluid dynamics model and the second functional parameter values for the second diagnostic invasive angiography image correspond to measured FFR or iFR pullback values.

In some exemplary embodiments, the first diagnostic image may correspond to an IVUS image and the second diagnostic image may correspond to a CT or invasive angiography image and the correspondence detection is performed based on first and second functional parameter values, such as pressure or flow distributions, that have been simulated by means of a fluid dynamics model for both, the first and the second diagnostic image.

In some exemplary embodiments, two CT or invasive angiography images may be co-registered—thereby performing correspondence detection—based on simulated functional parameter values. In some exemplary embodiments, the first diagnostic image may also correspond to a neuro MR image and the second diagnostic image may correspond to an ultrasound (US) image, whereby the first functional parameter values for the first diagnostic image may have been obtained using MR based flow measurements and the second functional parameter values for the second diagnostic image may have been obtained using Doppler flow measurements.

In other exemplary embodiments, the first diagnostic image may correspond to a CT image which is provided along with a simulated flow distribution as the first functional parameter values and registered to an intravascular US image provided along with Doppler flow measurement values as the second functional parameter values.

In some exemplary embodiments, the first diagnostic image may correspond to a CT image and the second diagnostic image may be an ICE image or TEE image and the correspondence detection may be performed by matching the first functional parameter values from Doppler flow measurements to the second functional parameter values derived from simulated flow distributions. Other combinations are likewise possible.

In some embodiments, the method further comprises obtaining one or more acquisition parameters used to acquire the first diagnostic image and/or the second diagnostic image, respectively, and correlating the one or more vessel positions along the vessel of interest as represented in the first and second diagnostic images, respectively, based on the one or more acquisition parameters.

In some embodiments, the acquisition parameters used to acquire the first diagnostic image and the second diagnostic image may be used as further information for performing the correspondence detection.

Acquisition parameters that may be used as such further information may particularly relate to the projection geometry, the heart phase and certain image features of the first and second diagnostic images, respectively. One or more of these acquisition parameters may hereby be combined in order to remove ambiguities and/or inaccuracies that may result from uncertainties that may be present when performing correspondence detection.

As an example, knowing the projection geometry, the orientation of the vessel of interest in the diagnostic image may be determined. Thus, the inherent error of misidentifying a vessel of interest in the first diagnostic image and/or the second diagnostic image when performing correspondence detection between these two can be reduced, as the projection geometry is known. It is thus possible to indicate how the vessel of interest should be represented in a diagnostic image for a particular projection geometry (or other factors exhibiting an influence on the vessel of interest and its representation in a diagnostic image in a similar manner), thereby allowing to accurately perform correspondence detection.

As stated, the acquisition parameters may be used to remove an uncertainty about the vessel identification. As a specific example, an FFR or iFR pullback measurement may have resulted in the acquisition of a plurality of pressure values that could be matched to either the pressure values that have been simulated for the left anterior descending (LAD) or the pressure values that have been simulated for the left circumflex artery (LCx). Knowledge of the projection geometry, in particular the projection angles of one or more invasive angiography images recorded along with the FFR or iFR pullback data may resolve whether the data is to be matched to the LAD or the LCx.

In some embodiments, the acquisition parameters may be used as further information to provide an initial starting point for the correspondence detection. As a specific example, knowledge about the projection geometry of one or more invasive angiography images and about the reconstruction geometry of one or more computed tomography (CT) angiography images may assist in performing initial co-registration of the image data from invasive angiography and CT angiography, respectively. This initial co-registration may then be used as the starting point for further correspondence detection, which then takes account of the (coronary) motion and potential miss-calibrations by matching e.g. pressure values from an FFR or iFR pullback measurement to respective simulated pressure values.

In some embodiments, further additional information, e.g. geometric information about the vessel of interest itself may also assist in providing a more accurate correspondence detection. In particular, further geometric information may allow to uniquely identify the vessel position in case multiple vessel positions may be matched to one particular functional parameter value. As an example of this, a pressure value obtained by an invasive measurement for one particular vessel position as visible in e.g. an invasive angiography image might be matched, as a first value, to two or more simulated pressure values at two or more vessel positions in a respective CT angiography image, the second values. That is, the vessel position in the CT angiography image that corresponds to the vessel position in the invasive angiography image is ambiguous. In that case, considering the vessel size as derivable from both, the invasive and the CT angiography image at the particular vessel positions allows to determine at which vessel position the vessel size as seen in the invasive angiography image matches the vessel size in the CT angiography image the best. This best match then allows to uniquely identify the particular vessel positions in the CT angiography image that is to be matched to the one vessel position in the invasive angiography image.

In some embodiments, the correlating the one or more vessel positions along the vessel of interest as represented in the first diagnostic image with the one or more vessel positions along the vessel of interest as represented in the second diagnostic image comprises determining a point to point correspondence for the one or more vessel positions along the vessel of interest as represented in the first and second diagnostic image, respectively.

In some embodiments, correspondence detection is performed by creating a point to point correspondence between the vasculature as shown in the first and the second diagnostic image by matching the first and second values of the corresponding functional information to one another. The point to point correspondence may then be used for multi-modality vessel modeling or multi-modality image visualization. In some embodiments, the point to point correspondence may particularly be achieved by determining the outflow, in particular the virtual outflow, and consecutively matching peaks of said (virtual) outflow as derived for the first diagnostic image and the second diagnostic image, respectively, to one another. In some embodiments, the point to point correspondence determination is further performed on the basis of additional information about the acquisition parameters, such as projection geometry or the like, as indicated herein above.

In some embodiments the first diagnostic image and/or the second diagnostic image may have been acquired using one or more of computed tomography (CT) angiography and/or invasive angiography and/or intravascular ultrasound (IVUS) imaging and/or magnetic resonance (MR) imaging and/or intracardiac echocardiography (ICE) and/or transesophageal echocardiography (TEE).

A variety of different (medical) imaging modalities can be envisioned for the purpose of the development. Further, a variety of functional parameter measurements may be acquired, such as by IVUS, TEE, ICE or the like.

In some embodiments, the method further comprises training a classifying device with a training dataset indicative of a correlation between a vessel of interest in the first diagnostic image and the second diagnostic image to obtain a classification result, and comparing the first value of the at least one functional parameter and the second value of the at least one functional parameter based on the classification result.

In some embodiments, the matching of the functional parameter values as derived for the first diagnostic image and the second diagnostic image, respectively, may also be performed by means of a machine learning algorithm, which may particularly be implemented as a trained classifier or in terms of a neural network. The machine learning algorithm, and in particular the classifier, may particularly be trained with a training dataset that is indicative of correlation of vessel of interest and functional parameter values. In some embodiments, the classifier uses the training result to perform the matching of the functional parameter values between the first and second diagnostic images, respectively, thereby generating the point to point correspondence.

In some embodiments, the method further comprises segmenting the vessel of interest as represented in the first diagnostic image and the second diagnostic image, respectively, and based on said segmenting, generating a physiological model of the vessel of interest.

In some embodiments, the first and second diagnostic image may be used for generating a physiological model of the vessel of interest. That is, upon correspondence detection having been performed, the information gathered by using different acquisition settings and/or different imaging modalities may be used to generate a more thorough physiological model of the vessel of interest. For this purpose, the vessel of interest as represented in the first and second diagnostic image may be segmented into a plurality of segments. On the basis of this segmentation, the physiological model of the vessel of interest may be generated, which comprises a geometric model of the vessel of interest, i.e. a geometric representation of the vessel of interest and/or the entire vasculature. This geometric model may typically be a two- or three-dimensional model, depending on the information that may be derived from the first and second diagnostic image. That is, if the first and/or second diagnostic image allow to derive information in three dimensions, the geometric model may be a three-dimensional model and if the first and/or second diagnostic image allow to derive information in two dimensions, the geometric model may be two-dimensional model. In other embodiments, where only two-dimensional information is available, the geometric model may also be a quasi three-dimensional model with the third dimension interpolated from the other two dimensions, According to a further aspect, an apparatus for analyzing diagnostic image data is provided, said apparatus comprising an input unit configured to obtain a first diagnostic image and a second diagnostic image of a vessel of interest in a patient's vasculature, a defining unit configured to define at least one determination position for the vessel of interest in the first diagnostic image and at least one corresponding determination position for the vessel of interest in the second diagnostic image, a determination unit configured to determine a first value for at least one functional parameter at the least one determination position for the first diagnostic image and a second value for the same at least one functional parameter at the corresponding determination position for the second diagnostic image and a correlation unit configured to correlate one or more vessel positions along the vessel of interest as represented in the first diagnostic image with one or more vessel positions along the vessel of interest as represented in the second diagnostic image based on a comparing of the first value of the at least one functional parameter and the second value of the at least one functional parameter. In some embodiments, the apparatus further comprises a modelling unit configured to generate a physiological model of the vessel of interest based on the first diagnostic image and the second diagnostic image.

In a further aspect, a computer program for controlling an apparatus according to the invention is provided, which, when executed by a processing unit, is adapted to perform the method steps according to the invention. In an even further aspect, a computer-readable medium is provided having stored thereon the above-cited computer program.

It shall be understood that the method of claim 1, the apparatus of claim 12, the computer program of claim 14 and the computer-readable medium of claim 15, have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

The illustration in the drawings is schematically. In different drawings, similar or identical elements are provided with the same reference numerals.

Figure 1:
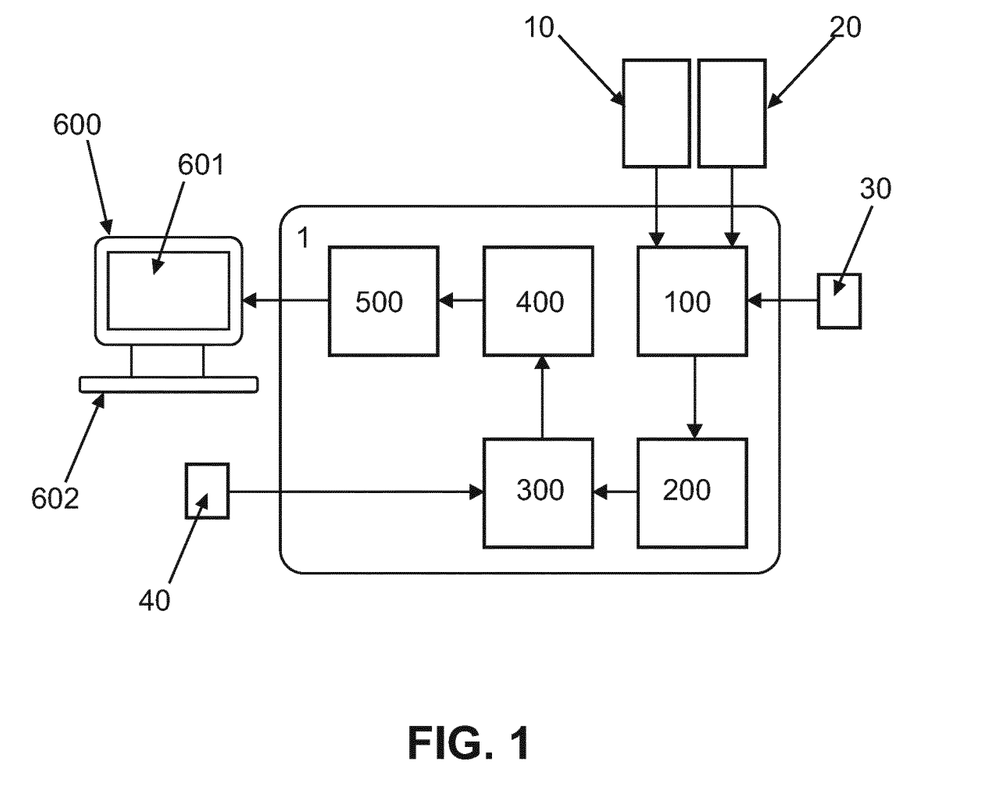
FIG. 1 schematically illustrates an apparatus for analyzing diagnostic image data according to an embodiment.

FIG. 1 represents schematically an exemplary embodiment of an apparatus 1 for analyzing diagnostic image data. The apparatus 1 comprises an input unit 100, a defining unit 200, a determination unit 300, a correlation unit 400, a modelling unit 500 and a display unit 600.

Input unit 100 is configured to receive a first diagnostic image 10 and a second diagnostic image 20. In the exemplary embodiment, the first diagnostic image 10 and the second diagnostic image 20 correspond to two-dimensional images which have been acquired using the same imaging modality, namely X-ray angiography, using different acquisition settings. In particular, the first diagnostic image 10 has been acquired with a different projection direction than the second diagnostic image 20. It shall be understood that, although in the specific embodiment according to FIG. 1, apparatus 1 is configured to receive two diagnostic images acquired by the same imaging modality, apparatus 1 is also configured to process a first diagnostic image 10 acquired using a first imaging modality and a second diagnostic image 20 acquired using a second imaging modality.

In the exemplary embodiment of FIG. 1, input unit 100 is further configured to receive data 30 indicating the respective acquisition settings used to acquire the first diagnostic image 10 and the second diagnostic image 20. In the exemplary embodiment according to FIG. 1, it is the input unit 100 that is further configured to obtain, from data 30, the acquisition parameters. In other embodiments, defining unit 200, determination unit 300 and/or correlation unit 400 may, alternatively or additionally, be configured to retrieve said acquisition parameters.

Input unit 100 is further configured to provide the first diagnostic image 10, the second diagnostic image 20 and the derived acquisition parameters to defining unit 200. Defining unit 200 is configured to receive the first diagnostic image 10 and the second diagnostic image 20 and to define at least one determination position for a respective vessel of interest as shown in the first diagnostic image 10 and the second diagnostic image 20. In the specific embodiment according to FIG. 1, defining unit 200 defines three determination positions along a longitudinal axis of the vessel of interest in the first diagnostic image 10 and three corresponding determination positions along a longitudinal axis of the vessel of interest in the second diagnostic image 20. It shall be understood that, in other embodiments, defining unit 200 may define more or less determination positions for the vessel of interest. Subsequently, defining unit 200 provides data indicating the defined determination positions along with the first diagnostic image 10 and the second diagnostic image 20 to determination unit 300.

Determination unit 300 is configured to receive, from defining unit 200, the first diagnostic image 10 and the second diagnostic image 20 as well as the data indicating the defined determination positions. Further, determination unit 300 is configured to receive intravascular measurement data 40 which, in the specific embodiment according to FIG. 1, corresponds to pressure pullback data that has been acquired by slowly pulling back a pressure wire through the vessel of interest.

Determination unit 300 is further configured to determine, based on the intravascular measurement data 40, respective values for at least one functional parameter at the respective determination positions. In the exemplary embodiment according to FIG. 1, determination unit 300 is configured to obtain a first pressure value for the first determination position, a first pressure value for the second determination position and a first pressure value for the third determination position from the first diagnostic image 10. Further determination unit 300 is configured to obtain a second pressure value for the first corresponding determination position, a second pressure value for the second corresponding determination position and a second pressure value for the third determination position from the second diagnostic image 20.

Determination unit 300 then provides data indicating the first and second pressure values obtained from the first diagnostic image 10 and the second diagnostic image 20 at the three respective determination positions, respectively, to correlation unit 400, along with the first diagnostic image 10, the second diagnostic image 20 and, optionally, the acquisition parameters.

Correlation unit 400 is configured to receive the data indicating the first and second pressure values, the first diagnostic image 10 and the second diagnostic image 20 and, optionally, the acquisition parameters. Correlation unit 400 then compares the first and second pressure values with one another in order to determine a correlation between a first plurality of vessel positions along a longitudinal axis of a vessel of interest as represented in the first diagnostic image 10 and a second plurality of vessel positions along a longitudinal axis of the same vessel of interest as represented in the second diagnostic image 20. In the specific embodiment according to FIG. 1, the correlation unit 400 particularly regards a pressure distribution as derived from the first and second pressure values and matches the pressure distribution as determined for the first pressure values to the pressure distribution as determined for the second pressure values. By doing so, correlation unit 400 may establish a point to point correspondence between the vessel of interest as shown in the first diagnostic image 10 and the vessel of interest as shown in the second diagnostic image 20. That is, it is determined for each vessel position of the vessel of interest in the first diagnostic image 10 the corresponding vessel position of the vessel of interest in the second diagnostic image 20. In the specific embodiment according to FIG. 1, the deriving of the point to point correspondence is further supported by the information about the acquisition parameters.

Upon registration of the vessel of interest in the first diagnostic image 10 to the vessel of interest in the second diagnostic image 20, the registered plurality of images is provided to modelling unit 500. Modelling unit 500 segments the vessel of interest in the first diagnostic image 10 and the second diagnostic image 20 and generates a physiological model of the vessel of interest. In the specific embodiment according to FIG. 1, the physiological model in particular comprises a geometric model allowing to derive the geometry of the vessel of interest. In some embodiments, the physiological model may also comprise a fluid dynamics model.

Modelling unit 500 is further configured to provide, upon generating the model, the generated model, optionally along with the first diagnostic image 10 and the second diagnostic image 20, to display unit 600 comprising a screen 601 and a user interface 602.

Display unit 600 is configured to generate a graphical representation of the physiological model and to present this graphical representation, optionally along with one or both of the first diagnostic image 10 and the second diagnostic image 20, to a user. In some embodiments, the user may interact with the model via user interface 602.

Figure 2:
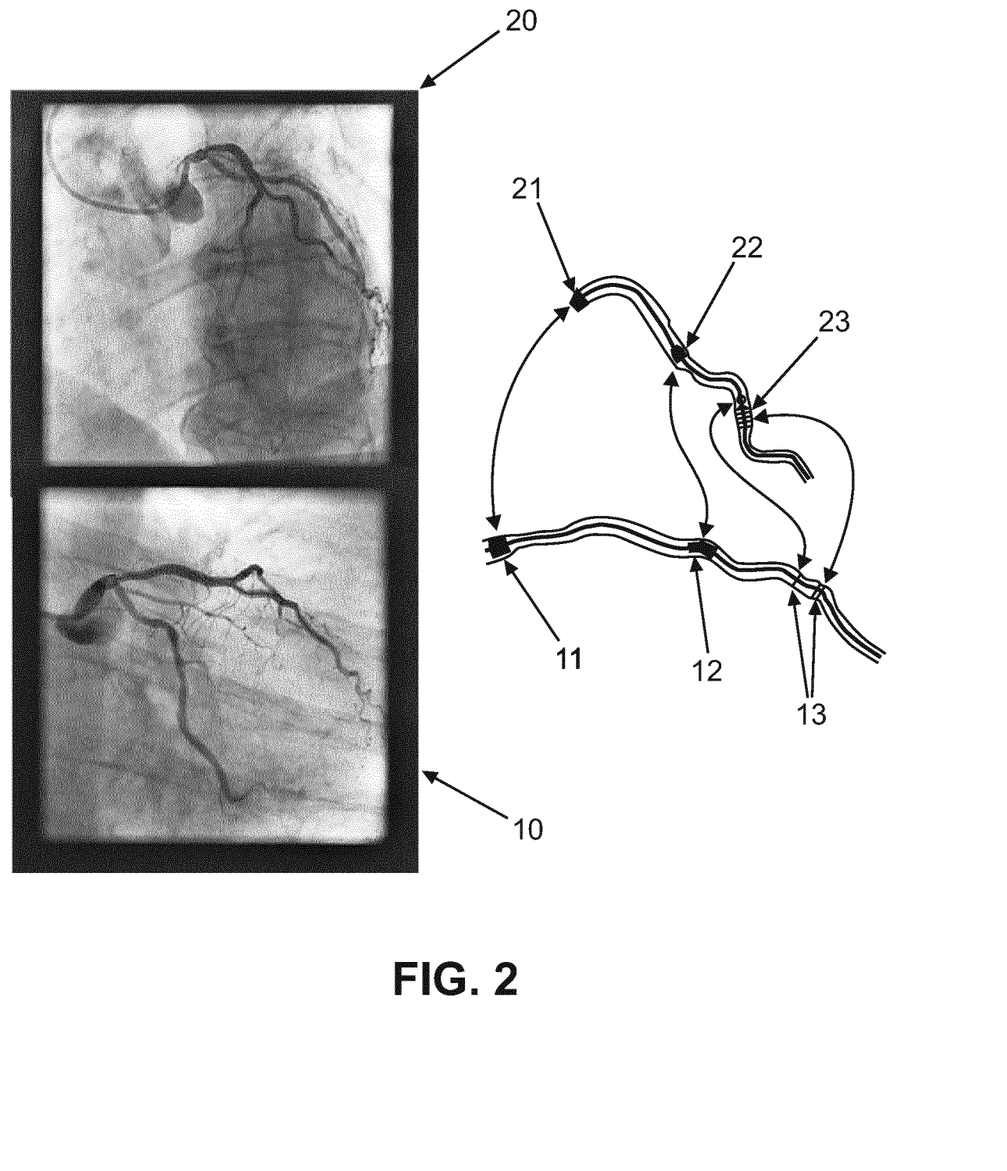
FIG. 2 schematically illustrates the correlation between the first and the second diagnostic image according to an embodiment.

FIG. 2 represents an approach for correlating a vessel of interest as represented in the first diagnostic image 10 and the second diagnostic image 20. In the specific embodiment according to FIG. 2, the first diagnostic image 10 and the second diagnostic image 20 correspond to coronary angiograms which have been acquired using different projection directions.

In the exemplary embodiment according to FIG. 2, a fluid dynamics model is generated from the first diagnostic image 10 and the second diagnostic image 20. The fluid dynamics model is then used to simulate the functional parameters for at least the determination positions 11, 12, 13, 21, 22 and 23 along the vessel of interest. In the specific embodiment according to FIG. 2, the fluid dynamics model is used to derive the virtual outflow through the vessel of interest at determination positions 11, 12 and 13 for diagnostic image 10 and at determination positions 21, 22 and 23 for diagnostic image 20. Subsequently, correlation unit 400 performs a matching of the peaks of virtual outflow through the vessel of interest, thereby providing a point to point reference between the at least two images.

Figure 3:
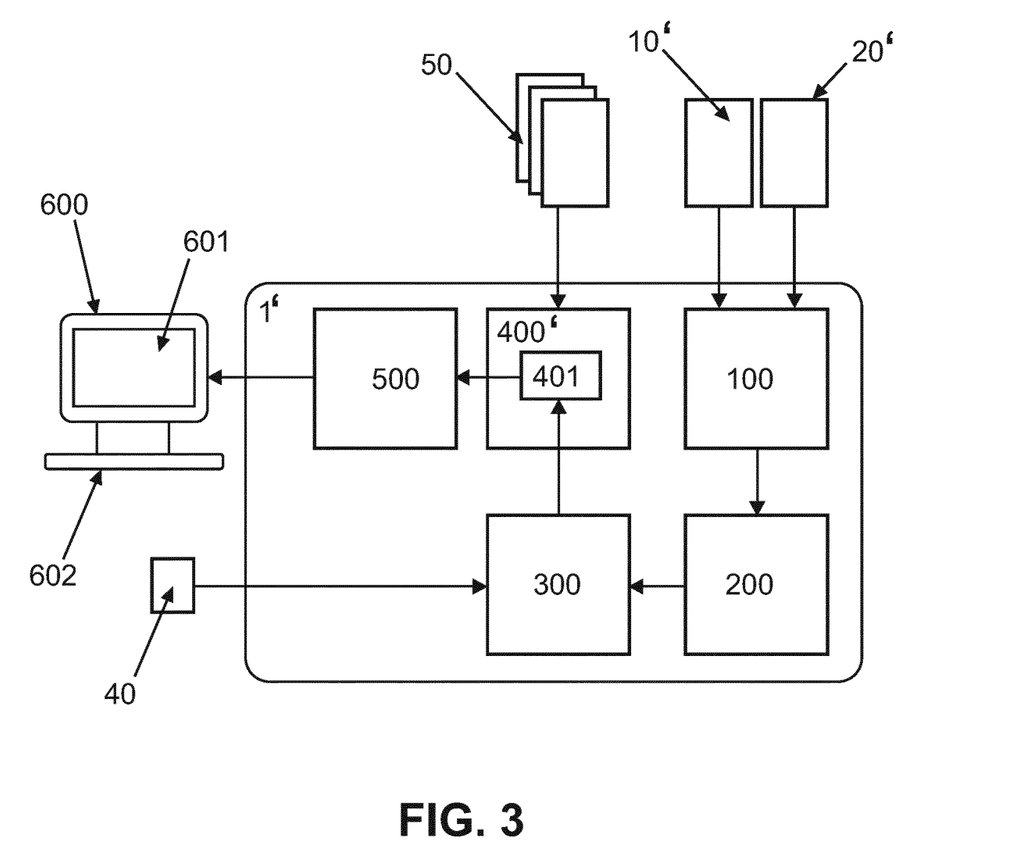
FIG. 3 represents a modification of the apparatus according to FIG. 1.

FIG. 3 schematically shows apparatus 1' which is a modification of the apparatus 1 according to FIG. 1. Like components of the apparatus 1' compared to apparatus 1 are referenced by the same reference signs. That is, apparatus 1' also comprises an input unit 100, a defining unit 200, a determination unit 300, a modelling unit 500 and a display unit 600. Apparatus 1' further comprises a correlation unit 400' comprising a classifying device 401.

In order to avoid repetitions, in the following, only the differences between apparatus 1 and apparatus 1' are explained in detail. That is, input unit 100, defining unit 200 and determination unit 300 as well as modelling unit 500 and display unit 600 are configured as described in relation to FIG. 1.

In the specific embodiment according to FIG. 3, input unit 100 receives a first diagnostic image 10' that has been acquired by a first imaging modality, which, in the specific case of FIG. 2, corresponds to X-ray angiography. Further, input unit 100 receives a second diagnostic image 20' that has been acquired using a second imaging modality, which, in this specific case, corresponds to magnetic resonance imaging. It shall be understood that, although the apparatus 1' is configured to receive (and process) a first diagnostic image 10' and a second diagnostic image 20' acquired with two different imaging modalities, apparatus 1' could likewise receive and process a first diagnostic image 10 and a second diagnostic image 20 as acquired with one particular imaging modality.

The first diagnostic image 10' and the second diagnostic image 20' are processed as described in relation to FIG. 1. The difference between apparatus 1 according to FIG. 1 and apparatus 1' according to FIG. 3 resides in the correlation unit 400'. In contrast to the embodiment according to FIG. 1, correlation unit 400' according to FIG. 2 comprises a classifying device 401. Classifying device 401 has been trained by training dataset 50, which is typically provided to classifying device 401 prior to correlation, with a correspondence between at least one functional parameter along a vessel of interest as represented in a first diagnostic image 10 and a second diagnostic image 20.

In the specific embodiment according to FIG. 3, the classifying device receives the first diagnostic image 10 and the second diagnostic image 20 and classifies the two diagnostic images in order to establish the point to point correspondence. Upon registration of the first diagnostic image 10 to the second diagnostic image 20, the registered diagnostic images are provided to modelling unit 500 which then proceeds as described in relation to FIG. 1.

Figure 4:
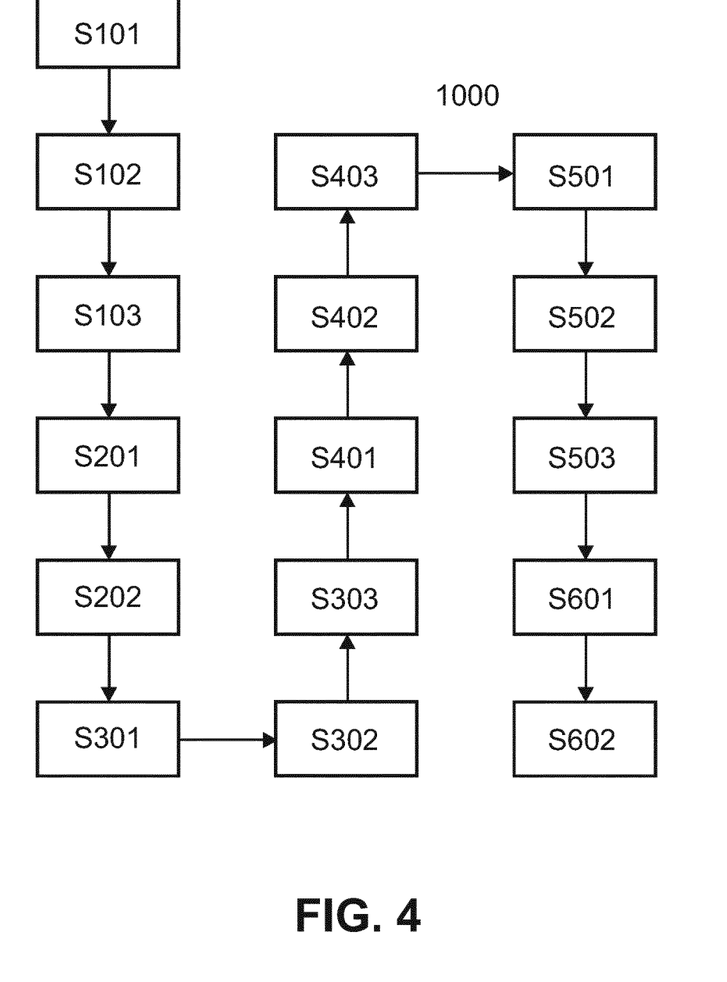
FIG. 4 shows a flow chart of a method for analyzing diagnostic image data according to an embodiment.

FIG. 4 schematically represents a method 1000 for analyzing diagnostic image data as executed by apparatus 1. In step S101, input unit 100 receives the first diagnostic image 10 and the second diagnostic image 20. In step S102, input unit 100 further receives data 30 indicative of the acquisition settings used for acquiring the first diagnostic image 10 and the second diagnostic image 20. In step S103, the input unit 100 derives the relevant acquisition parameters from data 30 and provides the first diagnostic image 10 and the second diagnostic image 20 along with the acquisition parameters derived from data 30 to defining unit 200.

In step S201, defining unit 200 receives the first diagnostic image 10 and the second diagnostic image 20 along with the acquisition parameters. In step S202, defining unit 200 defines at least one determination position for a respective vessel of interest as shown in the first diagnostic image 10 and the second diagnostic image 20. In the specific embodiment according to FIG. 4, defining unit 200 again defines three determination positions along the vessel of interest in the first diagnostic image 10 and three corresponding determination positions along the vessel of interest in the second diagnostic image 20. Defining unit 200 then provides the first diagnostic image 10 and the second diagnostic image 20 and the data indicating the defined determination positions to determination unit 300.

In step S301, determination unit 300 receives the first diagnostic image 10, the second diagnostic image 20 and the data indicating the determination positions from determination unit 300 and further receives intravascular measurement data 40 indicative of at least one functional parameter. In step S302, determination unit 300 derives, based on the intravascular measurement data 40, respective values for the at least one functional parameter at the respective determination positions. In the exemplary embodiment according to FIG. 4, determination unit 300 particularly derives a first pressure value for the first determination position, a first pressure value for the second determination position and a first pressure value for the third determination position from the first diagnostic image 10 and derives a second pressure value for the first corresponding determination position, a second pressure value for the second corresponding determination position and a second pressure value for the third corresponding determination position from the second diagnostic image 20.

In step S303, determination unit 300 provides the first diagnostic image 10, the second diagnostic image 20 and, optionally, the acquisition parameter as indicated by data 30 along with data indicating the first and second pressure values obtained from the first diagnostic image 10 and the second diagnostic image 20 at the three corresponding determination positions to correlation unit 400.

In step S401, correlation unit 400 receives the first diagnostic image 10 and the second diagnostic image 20 along with the data indicating the first and second pressure values, and, optionally, the acquisition parameters. In step S402, correlation unit 400 compares the first and second pressure values with one another and, in step S403, determines a correlation between a first plurality of vessel positions along the vessel of interest as represented in the first diagnostic image 10 and a second plurality of vessel positions the same vessel of interest as represented in the second diagnostic image 20 and thus performs a vessel registration for the vessel of interest. Subsequently, correlation unit 400 provides the registered plurality of images to modelling unit 500.

In step S501, modelling unit 500 receives the registered plurality of images and segments, in step S502, the vessel of interest in the first diagnostic image 10 and the second diagnostic image 20. In step S503, modelling unit 500 generates a physiological model of the vessel of interest and provides the generated model, optionally along with the first diagnostic image 10 and the second diagnostic image 20, to display unit 600.

In step S601, display unit 600 then generates a graphical representation of the physiological model, optionally including the first diagnostic image 10 and/or second diagnostic image 20. In step S602, display unit 600 then displays the graphical representation to a user, upon which display a user may interact with the displayed information.

Although in the above embodiments, the first diagnostic image and the second diagnostic image have been acquired using X-ray angiography with different acquisition settings, it shall be understood that the first diagnostic image and the second diagnostic image may also be acquired using a different imaging modality, such as invasive angiography, neuro MR imaging, US imaging, CT imaging, ICE imaging, TEE imaging or the like.

Although in the above embodiments, the functional parameter values correspond to pressure values, in other embodiments, further functional (dynamic) parameter values may be used such as flow, vascular resistance or the like.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the defining of the at least one determination position, the determining of the first and second value of the at least one functional parameter, the correlation the one or more vessel positions, the generating of a fluid dynamics model and the deriving, based on the fluid dynamics model, the first and second value of the at least one functional parameter, the generating of the physiological model, et cetera, performed by one or several units or devices can be performed by any other number of units or devices. These procedures, particularly the control of the apparatus for analyzing the diagnostic image data in accordance with the control method carried out by to respective apparatus controller, can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a method for analyzing diagnostic image data comprising: obtaining a first diagnostic image and a second diagnostic image of a vessel of interest in a patient's vasculature, defining at least one determination position for the vessel of interest in the first diagnostic image and at least one corresponding determination position for the vessel of interest in the second diagnostic image, determining a first value for at least one functional parameter at the least one determination position for the first diagnostic image and a second value for the same at least one functional parameter at the corresponding determination position for the second diagnostic image, correlating one or more vessel positions along the vessel of interest as represented in the first diagnostic image with one or more vessel positions along the vessel of interest as represented in the second diagnostic image based on a comparing of the first value of the at least one functional parameter and the second value of the at least one functional parameter.

The invention claimed is:

1. A method for analyzing diagnostic image data, the method comprising:
   obtaining a first diagnostic image of a vessel of interest in a patient's vasculature and a second diagnostic image of the vessel of interest in the patient's vasculature, wherein a first visual appearance of the vessel of interest in the first diagnostic image and a second visual appearance of the vessel of interest in the second diagnostic image are different from one another such that one or more vessel positions are represented differently in the first diagnostic image and the second diagnostic image,
   defining at least one determination position for the vessel of interest in the first diagnostic image and at least one corresponding determination position for the vessel of interest in the second diagnostic image,
   determining a first value for at least one functional parameter at the at least one determination position in the first diagnostic image and a second value for the at least one functional parameter at the at least one corresponding determination position in the second diagnostic image, and
   determining a correlation between the first visual appearance of the vessel of interest and the different, second visual appearance of the vessel of interest based on comparing the first value of the at least one functional parameter at the at least one determination position and the second value of the at least one functional parameter at the at least one corresponding determination position, wherein the correlation is between the one or more vessel positions as represented in the first diagnostic image with the one or more vessel positions as represented in the second diagnostic image.

2. The method according to claim 1, wherein the obtaining of the first diagnostic image and the second diagnostic image comprises:
   acquiring the first diagnostic mage by a first diagnostic imaging modality using a first acquisition setting, and
   acquiring the second diagnostic image by the first diagnostic imaging modality using a second acquisition setting, different from the first acquisition setting.

3. The method according to the claim 1, wherein the obtaining of the first diagnostic image and the second diagnostic image comprises:
   acquiring the first diagnostic image by a first diagnostic imaging modality, and
   acquiring the second diagnostic image by a second diagnostic imaging modality, different from the first diagnostic imaging modality.

4. The method according to claim 3, wherein the first diagnostic imaging modality corresponds to a non-invasive diagnostic imaging modality and the second diagnostic imaging modality corresponds to an invasive diagnostic imaging modality.

5. The method according to claim 1, wherein the determining of the first value and the second value of the at least one functional parameter comprises:
   acquiring intravascular measurement data for the vessel of interest, and
   deriving, based on the intravascular measurement data, the first value and the second value of the at least one functional parameter at the at least one determination position.

6. The method according to claim 1, wherein the determining of the first value and the second value of the at least one functional parameter comprises:
   generating a fluid dynamics model for the vessel of interest, and
   deriving, based on the fluid dynamics model, the first value and the second value of the at least one functional parameter at the at least one determination position.

7. The method according to claim 1, further comprising:
   obtaining one or more acquisition parameters used to acquire at least one of the first diagnostic image or the second diagnostic image, respectively, and
   correlating the one or more vessel positions as represented in the first diagnostic image with the one or more vessel positions as represented in the second diagnostic image based on the one or more acquisition parameters.

8. The method according to claim 1, wherein the the determining the correlation comprises:
   determining a point to point correspondence along the vessel of interest between the first diagnostic image and the second diagnostic image.

9. The method according to claim 1, wherein at least one of the first diagnostic image or the second diagnostic image is acquired using one or more of: computed tomography angiography, invasive angiography, intravascular ultrasound imaging, magnetic resonance imaging, intracardiac echocardiography, or transesophageal echocardiography.

10. The method according to claim 1, further comprising:
training a classifying device with a training dataset indicative of the correlation to obtain a classification result, and
comparing the first value of the at least one functional parameter and the second value of the at least one functional parameter based on the classification result.

11. The method according to claim 1, further comprising:
segmenting the vessel of interest as represented in the first diagnostic image and the second diagnostic image, respectively, and
based on the segmented vessel of interest, generating a physiological model of the vessel of interest.

12. The method according to claim 1, further comprising:
providing, to a display, an output associated with the correlation.

13. A system for analyzing diagnostic image data, the system comprising:
at least one processor configured to:
obtain a first diagnostic image of a vessel of interest in a patient's vasculature and a second diagnostic image of the vessel of interest in the patient's vasculature, wherein a first visual appearance of the vessel of interest is different in the first diagnostic image and a second visual appearance of the vessel of interest in the second diagnostic image are different from one another such that one or more vessel positions are represented differently in the first diagnostic image and the second diagnostic image,
define at least one determination position for the vessel of interest in the first diagnostic image and at least one corresponding determination position for the vessel of interest in the second diagnostic image,
determine a first value for at least one functional parameter at the at least one determination position in the first diagnostic image and a second value for the at least one functional parameter at the at least one corresponding determination position in the second diagnostic image, and
determine a correlation between the first visual appearance of the vessel of interest and the different, second visual appearance of the vessel of interest based on a comparison of the first value of the at least one functional parameter at the at least one determination position and the second value of the at least one functional parameter at the at least one corresponding determination position, wherein the correlation is between the one or more vessel positions as represented in the first diagnostic image with the one or more vessel positions as represented in the second diagnostic image.

14. The system according to claim 13, wherein the at least one processor is further configured to:
generate a physiological model of the vessel of interest based on the first diagnostic image and the second diagnostic image.

15. The system according to claim 13, wherein, to obtain the first diagnostic image and the second diagnostic image, the at least one processor is further configured to:
acquire the first diagnostic mage by a first diagnostic imaging modality using a first acquisition setting, and
acquire the second diagnostic image by the first diagnostic imaging modality using a second acquisition setting, different from the first acquisition setting.

16. The system according to claim 13, wherein, to obtain the first diagnostic image and the second diagnostic image, the at least one processor is further configured to:
acquire the first diagnostic image by a first diagnostic imaging modality, and
acquire the second diagnostic image by a second diagnostic imaging modality, different from the first diagnostic imaging modality.

17. The system according to claim 13, wherein, to determine the first value and the second value of the at least one functional parameter, the at least one processor is further configured to:
generate a fluid dynamics model for the vessel of interest, and
derive, based on the fluid dynamics model, the first value and the second value of the at least one functional parameter at the at least one determination position.

18. The system according to claim 13, wherein, to determine the correlation, the at least one processor is further configured to:
determine a point to point correspondence along the vessel of interest between the first diagnostic image and the second diagnostic image.

19. The system according to claim 13, wherein the at least one processor is further configured to:
train a classifying device with a training dataset indicative of the correlation to obtain a classification result, and
compare the first value of the at least one functional parameter and the second value of the at least one functional parameter based on the classification result.

20. The system according to claim 13, wherein the at least one processor is further configured to:
segment the vessel of interest as represented in the first diagnostic image and the second diagnostic image, respectively, and
based on the segmented vessel of interest, generate a physiological model of the vessel of interest.

21. The system according to claim 13, wherein the at least one processor is further configured to:
provide, to a display, an output associated with the correlation.

22. A non-transitory computer-readable storage medium having stored a computer program comprising instructions, which, when executed by a processor, cause the processor to:
obtain a first diagnostic image of a vessel of interest in a patient's vasculature and a second diagnostic image of the vessel of interest in the patient's vasculature, wherein a first visual appearance of the vessel of interest in the first diagnostic image and a second visual appearance of the vessel of interest in the second diagnostic image are different from one another such that one or more vessel positions are represented differently in the first diagnostic image and the second diagnostic image,
define at least one determination position for the vessel of interest in the first diagnostic image and at least one corresponding determination position for the vessel of interest in the second diagnostic image,
determine a first value for at least one functional parameter at the at least one determination position in the first diagnostic image and a second value for the at least one functional parameter at the at least one corresponding determination position in the second diagnostic image, and determine a correlation between the first visual appearance of the vessel of interest and the different, second visual appearance of the vessel of interest based on a comparison of the first value of the at least one functional parameter at the at least one determination position and the second value of the at least one functional parameter at the at least one corresponding determination position, wherein the correlation is between the one or more vessel positions as represented in the first diagnostic image with the one or more vessel positions as represented in the second diagnostic image.

23. The non-transitory computer-readable storage medium according to claim 14, wherein the instructions further cause the processor to:

provide, to a display, an output associated with the correlation.

* * * * *